(12) United States Patent  
Carpentier et al.

(10) Patent No.: US 8,492,493 B2  
(45) Date of Patent: Jul. 23, 2013

(54) STERICALLY EMCUMBERED BIDENTATE AND TRIDENTATE NAPHTHOXY-IMINE METALLIC COMPLEXES

(75) Inventors: Jean-François Carpentier, Acigne (FR); Evgueni Kirillov, Rennes (FR); Abbas Razavi, Mons (BE)

(73) Assignees: Total Petrochemicals Research Feluy, Seneffe (Feluy) (BE); Centre National de la Recherche Scientifique (CNRS), Paris (FR)

( * ) Notice: Subject to any disclaimer, the term of this patent is extended or adjusted under 35 U.S.C. 154(b) by 310 days.

(21) Appl. No.: 12/990,010

(22) PCT Filed: Apr. 24, 2009

(86) PCT No.: PCT/EP2009/054947  
§ 371 (c)(1),  
(2), (4) Date: Jan. 14, 2011

(87) PCT Pub. No.: WO2009/133026  
PCT Pub. Date: Nov. 5, 2009

(65) Prior Publication Data  
US 2011/0105704 A1    May 5, 2011

(30) Foreign Application Priority Data  
Apr. 28, 2008  (EP) .................... 08290410

(51) Int. Cl.  
C08F 4/69  (2006.01)  
C08F 4/72  (2006.01)  
C08F 4/78  (2006.01)  
C07F 11/00  (2006.01)

(52) U.S. Cl.  
USPC ........... 526/172; 526/170; 526/161; 526/160; 526/169; 526/348; 526/348.5; 526/352; 556/57

(58) Field of Classification Search  
USPC .................... 526/172, 160, 161, 169; 556/57  
See application file for complete search history.

(56) References Cited

U.S. PATENT DOCUMENTS  
6,309,997 B1 * 10/2001 Fujita et al. .................. 502/167

FOREIGN PATENT DOCUMENTS  
EP          1 426 385 A  *  6/2004  
EP          1426385          6/2004  
JP          2004-231859 A  *  8/2004

OTHER PUBLICATIONS

Kirillov et al. Organometallics, 2009, 28, 2401-2409.*  
Jones D J et al.: "Discovery of a new family of chormium ethylene polymerization catalysts using high throughput screening methodology" Chemical Communications—CHEMCOM, Royal Society of Chemistry, 2002, 1038-1039.  
Bluhm M E et al: "Chromium imine and amine complexes as homogeneous catalysts for the trimerisation and polymerisation of ethylene" Journal of Organometallic Chemistry, Elsevi, 2007, 692, 4377-4380.  
Mitani Makoto et al: "Fluorine-and trimethylsilyl-containing phenoxy-imine Ti complex for highly syndiotactic living polypropylenes with extremely high melting temperatures.", J. Am. Chem. Soc., 2002, 124, 7888-7889.  
Jiang et al: Titanium (IV) as an essential promoter in the asymmetric addition of diethylzinc to aldehydes catalyzed by aminonaphthol and imine ligands based on 3-substituted, J. Organomet. Chem., 2007, 692, 4377-4380.

* cited by examiner

*Primary Examiner* — Rip A. Lee (57) ABSTRACT

The present invention discloses post-metallocene complexes based on sterically encumbered bi- and tri-dentate naphthoxy-imine ligands. It also relates to the use of such post-metallocene complexes in the oligomerization of ethylene to selectively prepare vinyl-end capped linear alpha-olefins.

14 Claims, 10 Drawing Sheets

FIGURE 1 n = 1 or 2
R₁ = tBu, adamanthyl, anthracenyl, triptycenyl
Z = linker or non-coordinating R group (alkyl, aryl)
L¹ = pendant donor group (amino, pyridine, quinoline)
L² = donor molecule (acetonitrile, THF, pyridine)

STERICALLY EMCUMBERED BIDENTATE AND TRIDENTATE NAPHTHOXY-IMINE METALLIC COMPLEXES

CROSS-REFERENCE TO RELATED APPLICATIONS

This application claims the benefit of PCT/EP2009/054947, filed Apr. 24, 2009, which claims priority from EP 08290410.3, filed Apr. 28, 2008.

The present invention relates to the field of post-metallocene complexes based on sterically encumbered bi- and tri-dentate naphthoxy-imine ligands. It also relates to the use of such post-metallocene complexes in the oligomerisation of ethylene to selectively prepare vinyl-end capped linear alpha-olefins.

There is a need for new highly active alkene polymerisation catalyst systems based on post-metallocenes and a lot of research has been carried out in that field, such as reviewed for example in Gibson and Sptizmesser (Gibson, V. C.; Spitzmesser, S. K. in Chem. Rev. 2003, 103, 283) or in Ittel et al. (Ittel, S. D.; Johnson, L. K.; Brookhart, M. in Chem. Rev. 2000, 100, 1169 or in Britovsek et al. (Britovsek, G. J. P.; Gibson, V. C.; Wass, D. F. in Angew. Chem., Int. Ed. 1999, 38, 429).

Figure 1:
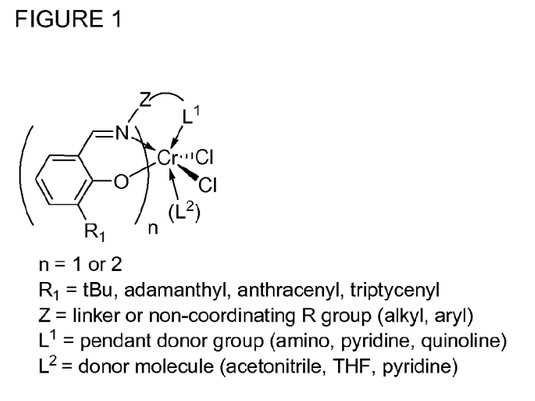
FIG. 1 represents various Cr(III) phenoxy-imino compounds disclosed in literature that are suitable for the oligomerisation or polymerisation of ethylene.

Among the plethora of newly disclosed catalytic systems, discrete group 3-6 metal complexes bearing various chelating aryloxide-based ligands have demonstrated astonishing performances in the polymerisation of ethylene and α-olefins. In particular, industry-relevant highly effective Cr(III) based phenoxy-imine systems were scrutinized by Gibson et al., such as disclosed for example in Jones et al. (Jones, D. J.; Gibson, V. C.; Green, S. M.; Maddox, P. J.; White, A. J. P.; Williams, D. J. in J. Am. Chem. Soc. 2005, 127, 11037) or in Meurs et al. (van Meurs, M.; Britovsek, G. J. P.; Gibson, V. C.; Cohen, S. A. in J. Am. Chem. Soc. 2005, 127, 9913) or in Gibson and O'Reilly (Gibson, V. C.; O'Reilly, R. K. US 20060258867A1) or in Gibson et al. (Gibson, V. C.; Mastroianni, S.; Newton, C.; Redshaw, C.; Solan, G. A.; White, A. J. P.; Williams, D. J. Dalton Trans. 2000, 1969). Typical metallic complexes of this family are represented in FIG. 1.

LIST OF FIGURES

FIG. 3 represents the $^1$H NMR spectrum of pro-ligand 2a.

FIG. 4 represents the molecular structure of pro-ligand 2a.

FIG. 7 represents the molecular structure of chromium complex 3a.

There is however still a need to develop new, very active catalyst systems having specific functionalities in order to tailor polymers with desired properties.

It is an aim of the present invention to prepare sterically encumbered ligands based on naphthoxy groups.

It is also an aim of the present invention to prepare very active catalyst systems for the oligomerisation and polymerisation of ethylene and alpha-olefins.

Any one of these aims is, at least partially, fulfilled by the present invention.

Accordingly, the present invention discloses a pro-ligand of formula I or its tautomeric form of formula I'

Wherein $R^1$, $R^3$, $R^4$, $R^5$, $R^6$ and $R^7$ are each independently selected from hydrogen, unsubstituted or substituted hydrocarbyl, or inert functional group, wherein two or more of said groups can be linked together to form one or more rings,
wherein Z is an atom selected from group 14 of the Periodic Table,
wherein each $R^2$ is independently selected from a substituted or unsubstituted aryl group having at most 8 carbon atoms, and/or an alkyl group, with the restriction that $Z(R^2)_3$ is a bulky group, at least as bulky as tertio-butyl,
wherein $R^8$ is a unsubstituted or substituted, aliphatic or aromatic hydrocarbyl group, possibly containing donor atoms such as halogens, or atoms selected from groups 15 and 16 of the periodic Table such as N, P, O, S.

Alternatively, $Z(R^2)_3$ can be a substituted aryl group.

Preferably $R^1$, $R^3$, $R^4$, $R^5$, $R^6$ and $R^7$ are each independently selected from hydrogen or alkyl groups having at most 6 carbon atoms, more preferably they all are hydrogen.

Preferably $R^8$ is $CH_2$-(2-pyridyl), alpha-quinoleine or $C_6F_5$.

Preferably, Z is C or Si, more preferably, it is Si.

Preferably all $R^2$ are the same and are substituted or unsubstituted phenyl group, or higher aromatic group (e.g. naphtyl), or alkyl. More preferably, each $R^2$ is unsubstituted phenyl group or a tertio-butyl group.

By inert functional group, is meant a group, other than hydrocarbyl or substituted hydrocarbyl, that is inert under the complexation conditions to which the compound containing said group is subjected. They can be selected for example from halo, ester, ether, amino, imino, nitro, cyano, carboxyl, phosphate, phosphonite, phosphine, phosphinite, thioether and amide. Preferably, they are selected from halo, such as chloro, bromo, fluoro and iodo, or ether of formula—OR* wherein R* is unsubstituted or substituted hydrocarbyl. After metallation of the ligand, an inert functional group must not coordinate to the metal centre.

The present ligand includes a naphtoxy group whereas most ligands disclosed in the prior art include a phenoxy group. The catalyst systems based on the present ligand that includes a naphtoxy group are more tolerant thanks to a combination of steric and/or electronic effects.

In addition, in the preferred ligands according to the present invention, Z is Si. Replacing C by Si also results in improving the tolerance of the catalyst system. For example, a catalyst system wherein Z is C sees its activity destroyed by the addition of acetonitrile, whereas there is no observed change either in activity or in oligomer/polymer properties for an equivalent catalyst system wherein Z is Si.

Several procedures have been tested in order to prepare the ligands of the present invention, most of them without success.

They can be prepared in good yield starting from 2-methoxynapthalene by a process that comprises the steps of:

a) providing 2-methoxynaphthalene of formula b) reacting with $(R^2)_3ZX'$, wherein $X'$ is an halogen, in the presence of sec-BuLi in a solvent to obtain a compound of formula c) reacting with N-bromosuccinimide to obtained a compound of formula d) reacting with DMF in the presence of 2 equivalents of tert-BuLi in a solvent to obtain a compound of formula e) deprotecting the compound obtained in step d) in order to obtain a compound of formula f) condensation of the compound obtained in step e) with amine $R^8$—$NH_2$ in the presence of catalytic amounts of about 1 mol-% of formic acid, to obtain a compound of formula I and its tautomeric form I'.

Figure 2:
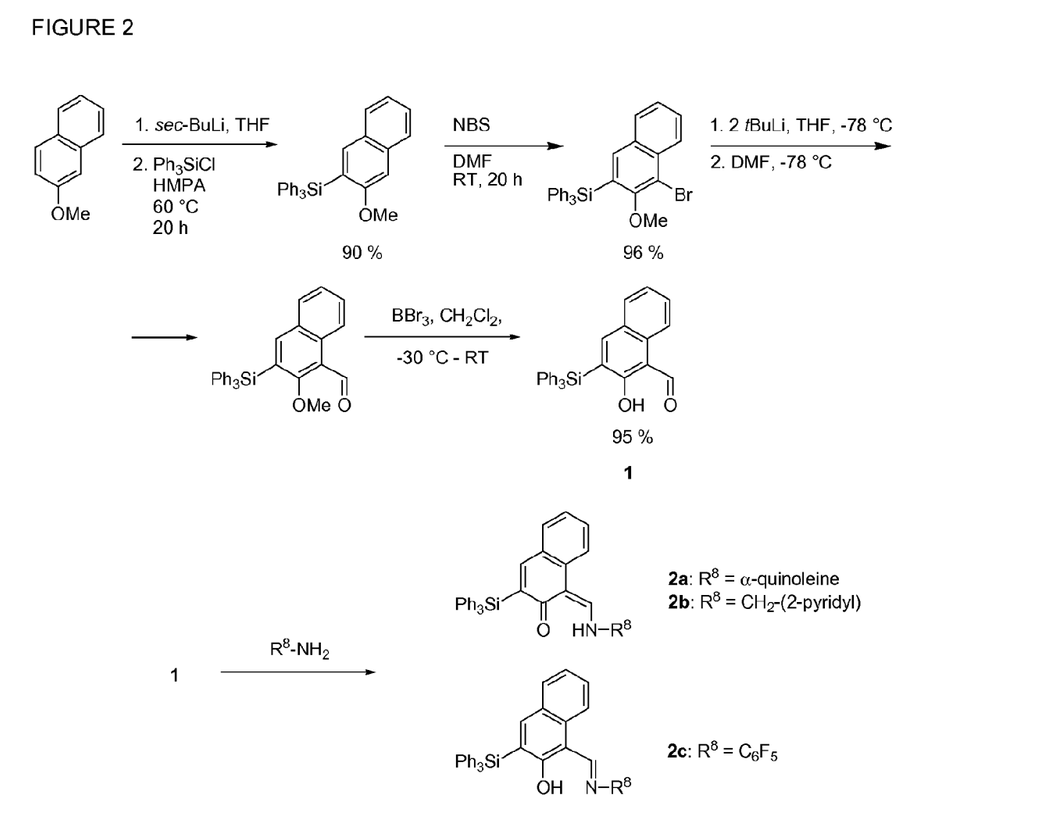
FIG. 2 represents the scheme used for the preparation of {ONN}H and {ON}H pro-ligands.

The method of preparation can be summarised in the scheme presented in FIG. 2. Deprotection step e) can be carried out for example by treatment with $BBr_3$.

The acid of step f) can be selected for example from HCOOH or PTSA.

The invention also discloses metallic complexes of general formula II (II)

Metallic complexes II result from the complexation of pro-ligand I (I') with metallic salts $MX_n$ in a solvent, wherein M is a metal Group 6 of the periodic Table, wherein each X is the same or different and is an alkyl, benzyl substituted or not, aryl substituted or not, amido, alkoxide, and/or halide such as Cl, Br or I, and wherein $L^2$ is a solvent such as for example acetonitrile, THF or pyridine, preferably acetonitrile.

Preferably X are either all the same and are Br, or one X is para-tolyl and the other X is Br.

Preferably M is chromium.

Preferably one equivalent of metallic salt is used per naphthoxy-imine complex.

The metallation reaction is carried out at a temperature of from −80° C. to a temperature of +25° C. and for a period of time of 1 to 18 hours.

The present invention also discloses a catalyst system comprising the Group 6 metal single-site catalyst component of formula II and an activating agent having an alkylating/ionising action.

Suitable activating agents are well known in the art. The activating agent can be an aluminium alkyl represented by formula $AlR^+{}_nX_{3-n}$ wherein $R^+$ is an alkyl having from 1 to 20 carbon atoms and X is a halogen, in combination with $[Ph_3C]$ $[B(C_6F_5)_4]$. The preferred aluminium alkyls are triisobutylaluminium (TIBAL) or triethylaluminium (TEAL). Aluminium alkyls are used in combination with trityl.

Alternatively, it can be aluminoxane and comprise oligomeric linear and/or cyclic alkyl aluminoxanes represented by formula for oligomeric, linear aluminoxanes and by formula for oligomeric, cyclic aluminoxane,
wherein n is 1-40, preferably 1-20, m is 3-40, preferably 3-20 and R* is a $C_1$-$C_8$ alkyl group and preferably methyl or isobutyl.

Preferably, the activating agent is methylaluminoxane (MAO).

The amount of activating agent is selected to give an Al/M ratio of from 500 to 10000, preferably of from to 1000 to 5000. The amount of activating agent depends upon its nature.

Suitable boron-containing agents may also be used for activating Group 6 metal single-site catalyst component of formula II where $R^\$$ is an alkyl or benzyl group. These include for example a triphenylcarbenium boronate such as tetrakis(pentafluorophenyl)borato-triphenylcarbenium as described in EP-A-0427696, or those of the general formula $[L'-H]^+ [B Ar_1 Ar_2 X_3X_4]^-$ as described in EP-A-0277004 (page 6, line 30 to page 7, line 7).

The amount of boron-containing activating agent is selected to give a B/M ratio of from 0.5 to 5, preferably of about 1.

In another embodiment, according to the present invention, the single-site catalyst component of formula II may be deposited on a conventional support. Preferably, the conventional support is silica impregnated with MAO. Alternatively the support may also be an activating support such as fluorinated alumina silica.

The catalyst system may comprise an optional scavenger that may be selected from triethylaluminium, triisobutylaluminum, tris-n-octylaluminium, tetraisobutyldialuminoxane or diethylzinc.

The present invention discloses a method for the oligomerisation or the homo- or co-polymerisation of ethylene and alpha-olefins that comprises the steps of:
a) injecting the active catalyst system into the reactor;
b) injecting the monomer and optional comonomer either before or after or simultaneously with step a);
c) maintaining under polymerisation conditions;
d) retrieving the oligomers and/or polymer.

The pressure in the reactor can vary from 0.5 to 50 bars, preferably from 5 to 25 bars.

The polymerisation temperature can range from 10 to 100° C., preferably from 25 to 85° C.

The preferred monomer and optional comonomer can be selected from ethylene, propylene, 1-hexene. The preferred monomer is ethylene.

EXAMPLES

All experiments were performed under a purified argon atmosphere using standard Schlenk techniques, or in a glovebox. Solvents were distilled under nitrogen, from Na/benzophenone for THF and $Et_2O$, from $CaH_2$ for acetonitrile and from Na/K alloy for toluene and pentane. They were degassed thoroughly and stored under nitrogen prior to use. Deuterated solvents (benzene-$d_6$, toluene-$d_8$, THF-$d_8$; >99.5% D, Eurisotop) were vacuum-transferred from Na/K alloy into storage tubes. Starting materials were purchased from Acros, Strem and Aldrich. NMR spectra of complexes were recorded on Bruker AC-200, AC-300 and AM-500 spectrometers in Teflon-valved NMR tubes at 25° C. unless otherwise indicated. $^1H$ and $^{13}C$ chemical shifts are reported in ppm vs. $SiMe_4$ and were determined by reference to the residual solvent peaks. Assignment of resonances for organometallic complexes was made from $^1H$—$^{13}C$ HMQC and HMBC NMR experiments. Coupling constants are given in Hertz. Elemental analyses were performed by the Microanalytical Laboratory at the Institute of Chemistry of Rennes and are the average of two independent determinations.

I. Preparation of {ONN}H and {ON}H Ligands

A. Preparation of 3-methoxy-2naphthyl-triphenylsilane

A solution of 15.3 mL of sec-BuLi 1.3 M in hexane/cyclohexane (19.91 mmol) was added dropwise to a stirred solution of 3.0 g of 2-methoxynaphthalene (18.96 mmol) in 70 mL of tetrahydrofuran (THF) at a temperature of −30° C. and for a period of time of 15 min. After stirring overnight at room temperature, to the resultant tinted solution was added a solution of 5.87 g of $Ph_3SiCl$ (19.91 mmol) and 3.46 mL of hexamethylphosphoramide (HMPA) (19.88 mmol) in 50 mL of THF. The reaction mixture was heated at reflux for a period of time of 20 h, cooled and diluted with 500 mL of water. The organic part was extracted with 3 times 50 mL of $Et_2O$. The combined organic extracts were dried over $MgSO_4$, and evaporated. The crude residue was recrystallised from heptane and dried under vacuum to give 7.11 g of (3-methoxy-2-naphthyl)(triphenyl)silane (17.07 mmol) with a yield of 90%.

The NMR spectrum was as follows:
$^1H$ NMR (200 MHz, $CDCl_3$, 25° C.): δ 7.80 (m, 2H), 7.67 (m, 7H), 7.55-7.23 (m, 12H), 3.69 (s, 3H, $OCH_3$).

Anal. calcd. for $C_{29}H_{24}OSi$: C, 83.61; H, 5.81. Found: C, 82.15; H, 5.23.

B. Preparation of (4-bromo-3-methoxy-2-naphtyl)-triphenylsilane

A 150 mL Schlenk flask was charged with 4.68 g of (3-methoxy-2-naphthyl)(triphenyl)silane (11.23 mmol) and 2.20 g of N-bromosuccinimide (NBS) (12.36 mmol) under argon followed by addition of 10 mL of dimethylformamide (DMF). The resultant mixture was stirred overnight at room temperature, then diluted with 500 mL of water and extracted with 3 times 50 mL of $CH_2Cl_2$. The combined organic extracts were washed with 200 mL of water, brine and dried over $Na_2SO_4$. The product was purified by passing through short column (silica) using a mixture heptane:EtOAc in a ratio of 15:1 as eluent to afford 5.28 g of product as off-white solid (10.66 mmol) with a yield of 96%.

The NMR spectrum was as follows:
$^1$H NMR (200 MHz, $CDCl_3$, 25° C.): δ 8.29 (d, J=8.4 Hz, 1H), 7.80 (s, 1H), 7.66 (m, 8H), 7.52-7.27 (m, 10H), 3.18 (s, 3H, $OCH_3$).

Anal. calcd. for $C_{29}H_{23}BrOSi$: C, 70.30; H, 4.68. Found: C, 68.99; H, 4.56.

C. Preparation of 2-hydroxy-3-(triphenylsilyl)-1-naphthaldehyde (1)

A solution of 16.1 mL of tert-BuLi 1.5 M in pentane (24.10 mmol) was added dropwise to a stirred solution of 6.02 g of (4-bromo-3-methoxy-2naphtyl)-triphenylsilane (12.05 mmol) in 50 mL of $Et_2O$ at −78° C. The reaction mixture was stirred during 1.5 h at a given temperature and 30 min at 0° C. followed by addition of 0.94 mL of DMF. The resultant mixture was stirred overnight at room temperature and diluted with 200 mL of water. The organic part was extracted with $CH_2Cl_2$ (3×50 mL). The combined organic extracts were dried over $MgSO_4$. The resultant solution was transferred to a Schlenk flask under argon and a solution of 24.1 mL of $BBr_3$ 1M in $CH_2Cl_2$ (24.1 mmol) was added dropwise at −78° C. The reaction mixture was stirred overnight at room temperature, then carefully hydrolysed with 500 mL of water. The organic part was extracted with $CH_2Cl_2$ (3×50 mL). The combined organic extracts were dried over $MgSO_4$, and evaporated. The crude residue was recrystallised from methanol and dried under vacuum to give 5.44 g of 1 (12.63 mmol) with a yield of 95%.

The NMR spectrum was as follows:
$^1$H NMR (200 MHz, $CDCl_3$, 25° C.): δ 13.58 (s, 1H, OH), 10.88 (s, 1H, =CHO), 8.40 (d, J=8.4 Hz, 1H), 8.03 (s, 1H), 7.67 (m, 6H), 7.43 (m, 12H).

Anal. calcd. for $C_{29}H_{22}O_2Si$: C, 80.90; H, 5.15. Found: C, 80.17; H, 4.67.

D. Preparation of 1-[(quinolin-8-ylamino)methylene]-3-(triphenylsilyl)naphthalen-2-one (2a) as a stable tautomeric form of 1-[(quinolin-8-ylimino)methyl]-3-(triphenylsilyl)-2-naphthol To a stirred mixture of 1.09 g (2.53 mmol) of 1 and 0.37 g (2.53 mmol) of 8-aminoquinoline in 40 mL of methanol, was added formic acid (ca. 10 mg) at room temperature. The resultant mixture was stirred at reflux for 25 hours and the product precipitated as microcrystalline powder. The reaction mixture was transferred onto a Schott filter and filtered. The obtained orange solid was washed with cold methanol and dried under vacuum to give 0.77 g (1.38 mmol) of 2a with a yield of 55%.

The NMR spectra were as follows:
$^1$H NMR (500 MHz, $CD_2Cl_2$, 25° C.): δ 15.31 (d, J=11.1 Hz, 1H, NH), 9.31 (d, J=11.1 Hz, 1H, =CHN), 9.02 (dd, 1H), 8.26 (dd, 1H), 8.07 (d, J=8.2 Hz, 1H), 7.81 (m, 2H), 7.73 (m, 7H), 7.66 (m, 1H), 7.57-7.40 (m, 12H), 7.27 (m, 1H).
$^{13}$C NMR (125 MHz, $CD_2Cl_2$, 25° C.): δ 185.2, 151.7, 150.1, 146.4, 139.8, 137.4, 136.4, 136.1, 135.8, 135.0, 133.2, 130.0, 129.3, 129.2, 129.0, 127.7, 126.6, 126.5, 124.4, 123.5, 122.3, 118.3, 113.9, 108.2.

Figure 3:
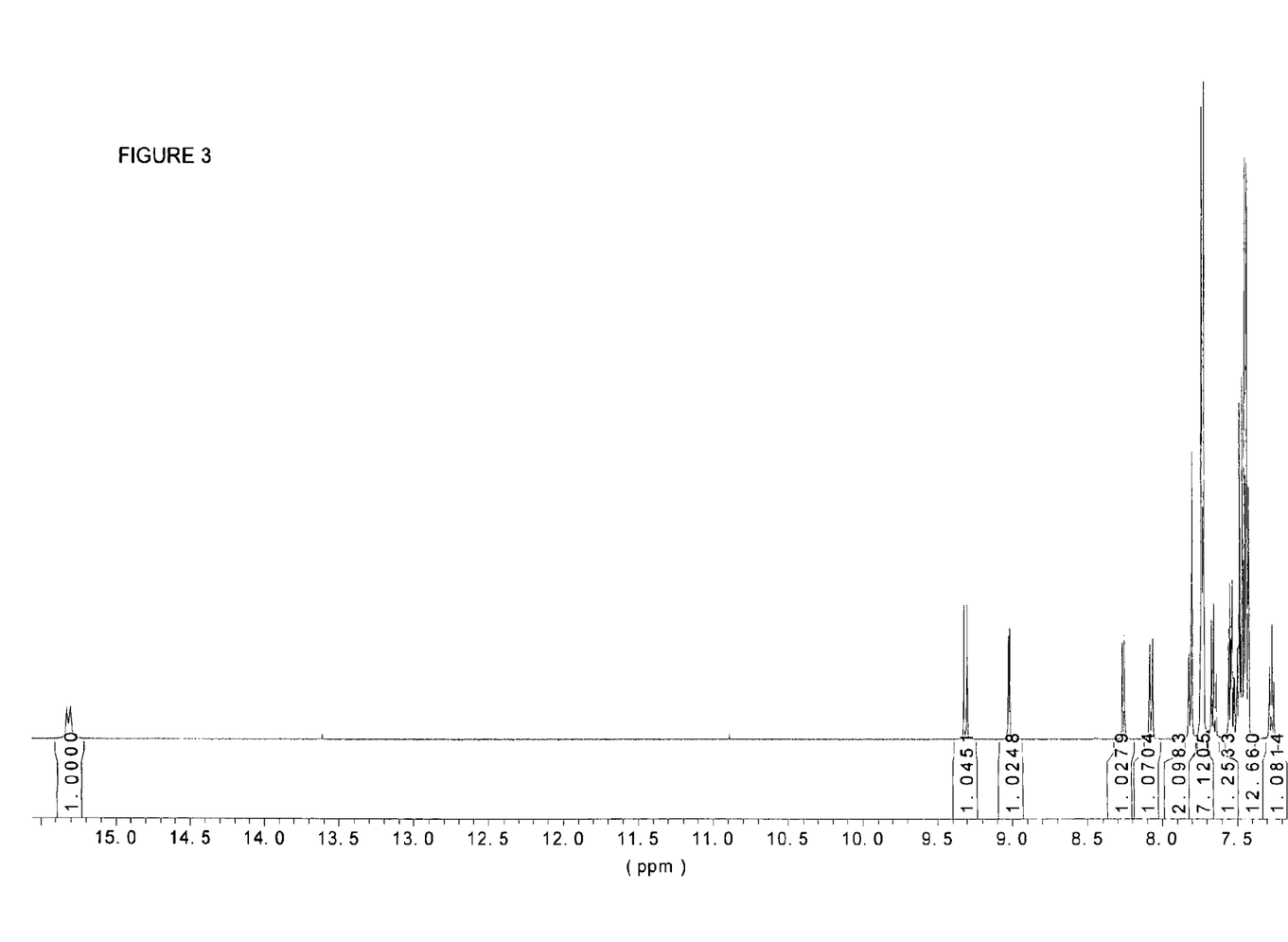

The $^1$H NMR of the pro-ligand is represented in FIG. 3.

Anal. calcd. for $C_{38}H_{28}N_2OSi$: C, 81.98; H, 5.07. Found: C, 81.04; H, 4.98.

Figure 4:
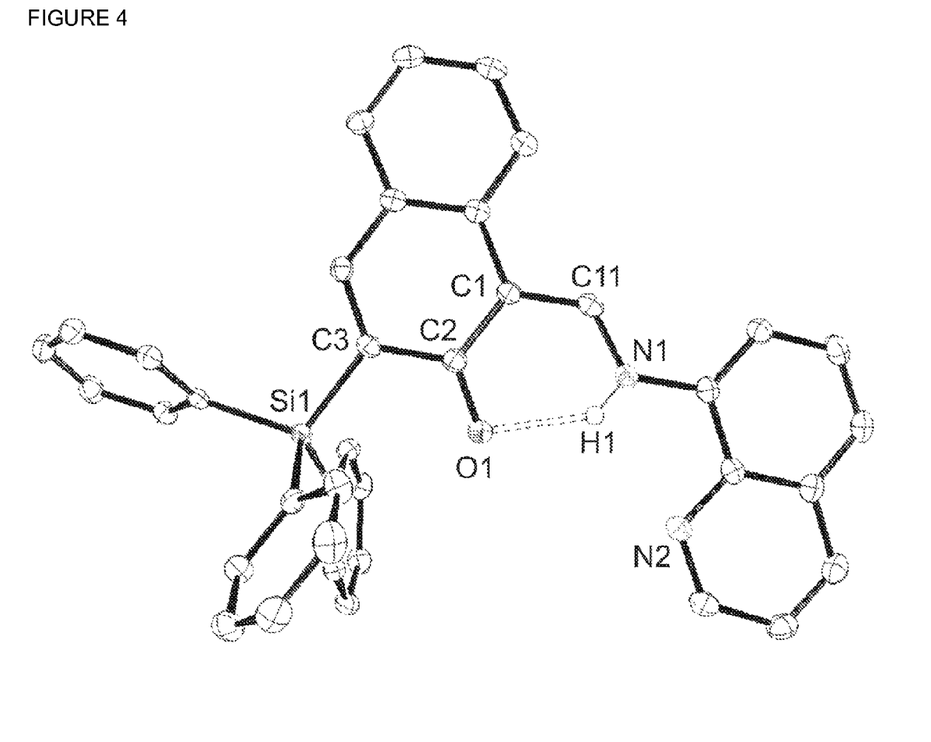

The molecular structure of this ligand can be seen in FIG. 4.

E. Preparation of 1-{[(pyridin-2-ylmethyl)amino]methylene}-3-(triphenylsilyl)naphthalen-2-one (2b) as a stable tautomeric form of 1-[(pyridin-2-ylmethyl)imino]methyl]-3-(triphenylsilyl)-2-naphthol Using the same protocol as described above, pro-ligand 2b was prepared in 0.78 g yield (1.50 mmol, 60%) from 1.08 g of 1 (2.51 mmol) and 0.29 g of 2-aminomethylpyridine (1.50 mmol).

The NMR spectra were as follows:
$^1$H NMR (500 MHz, $CD_2Cl_2$, 25° C.): δ 14.44 (br m, 1H, NH), 8.96 (d, J=8.8 Hz, 1H), 8.63 (dd, 1H), 7.95 (d, J=8.8 Hz, 1H), 7.79 (s, 1H), 7.70 (m, 1H), 7.67 (m, 6H), 7.60-7.35 (m, 11H), 7.32 (d, 1H), 7.25 (m, 1H), 7.23 (m, 1H), 4.88 (m, 2H, $CH_2Py$).
$^{13}$C NMR (125 MHz, $CD_2Cl_2$, 25° C.): δ 180.6, 158.6, 156.4, 149.8, 149.3, 136.9, 136.3, 135.6, 135.1, 131.5, 129.8, 129.2, 128.9, 127.7, 126.1, 122.8, 122.6, 121.9, 117.8, 106.1, 57.7.

Figure 5:
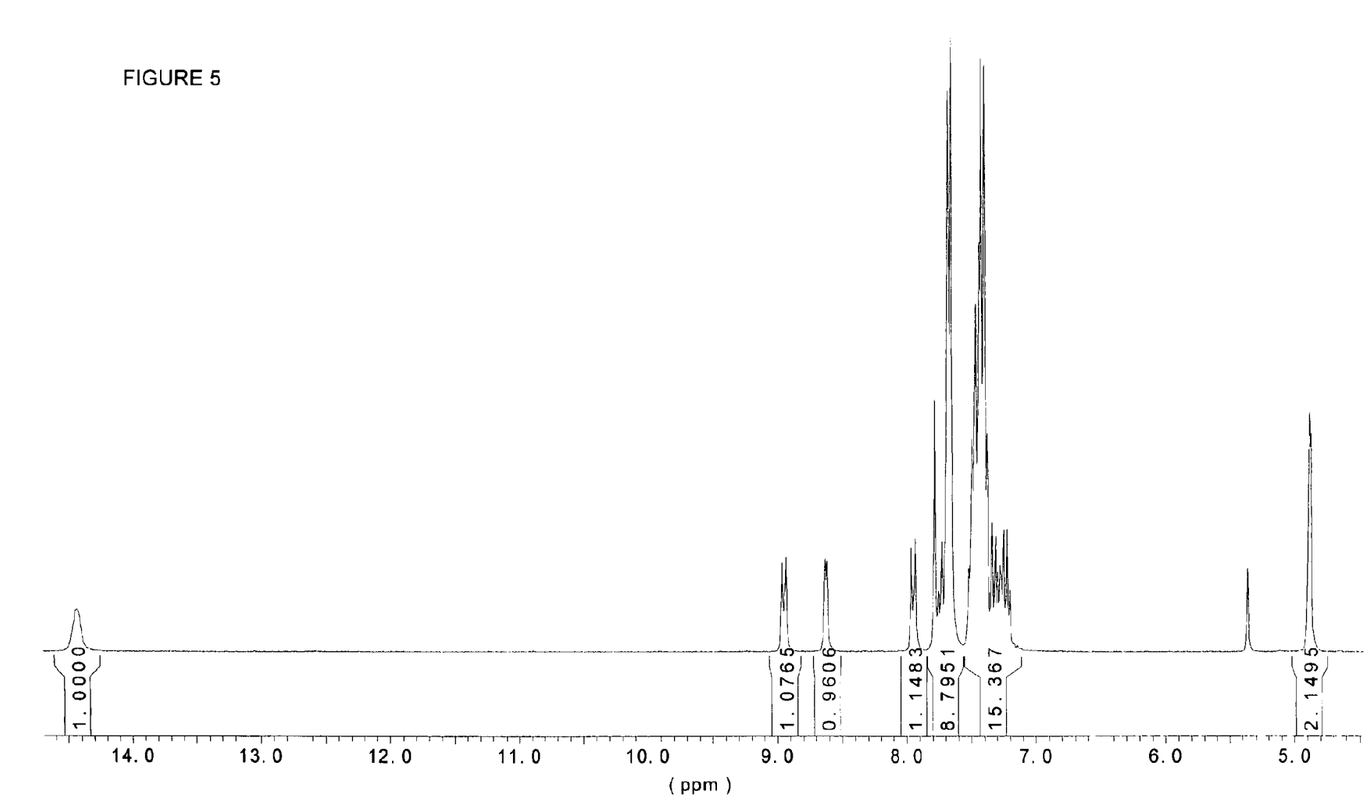
FIG. 5 represents the $^1$H NMR spectrum of pro-ligand 2b.

The $^1$H NMR of the pro-ligand is represented in FIG. 5.
Anal. calcd. for $C_{35}H_{28}N_2OSi$: C, 80.73; H, 5.42. Found: C, 79.94; H, 5.00.

F. Preparation of 1-[(pentafluorophenyl)imino]methyl}-3-(triphenylsilyl)-2-naphthol (2c)

Pro-ligand 2c was synthesised by condensation of 1.04 g of 1 (2.42 mmol) and 0.44 g of pentafluoro-aniline (2.42 mmol) in toluene at reflux for 40 hours in the presence of PTSA (ca. 5% w), using Dean-Stark apparatus. The reaction mixture was evaporated and the residue was recrystallized from methanol to give 2c in 0.93 g yield (1.57 mmol, 65%).

The NMR spectra were as follows:
$^1$H NMR (500 MHz, $CDCl_3$, 25° C.): δ 14.49 (s, 1H, OH), 9.76 (s, 1H), 8.13 (d, J=8.5 Hz, 1H), 7.96 (s, 1H), 7.71 (d, J=6.7 Hz, 6H), 7.69 (d, J=10.2 Hz, 1H), 7.62 (t, J=10.2 Hz, 1H), 7.52-7.30 (m, 10H).
$^{13}$C NMR (125 MHz, $CDCl_3$, 25° C.): δ 168.5, 165.9, 148.1, 136.4, 134.2, 134.0, 130.2, 129.6, 129.4, 127.9, 127.7, 126.3, 123.9, 118.9, 108.8 (signals from the Ph group were hardly observed).
$^{19}$F NMR (188 MHz, $CDCl_3$, 25° C.): δ-152.4 (m, 2F), −159.1 (t, 1F), −162.8 (m, 2F).

Figure 6:
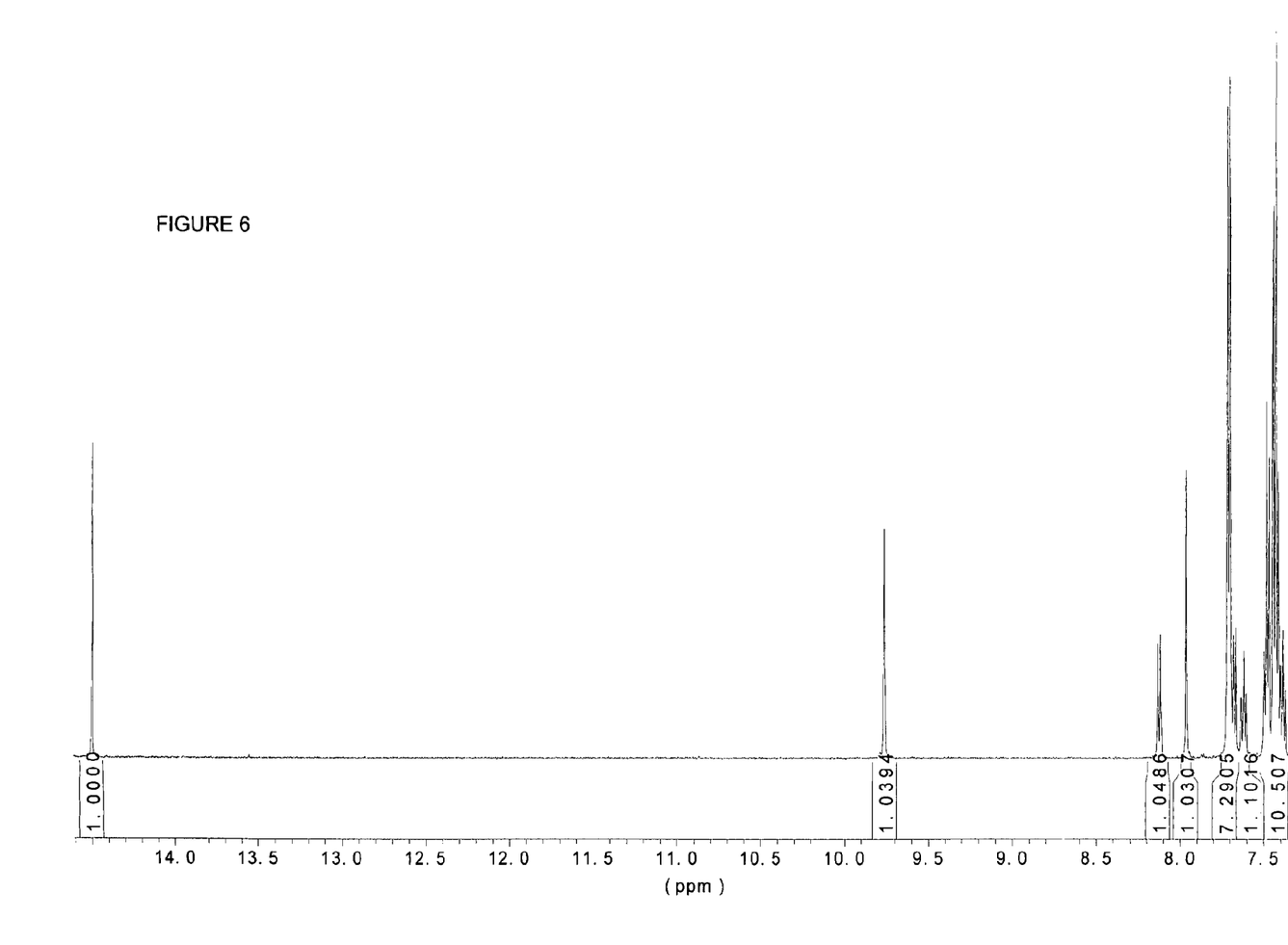
FIG. 6 represents the $^1$H NMR spectrum of pro-ligand 2c.

The $^1$H NMR of the pro-ligand is represented in FIG. 6.
Anal. calcd. for $C_{35}H_{22}F_5NOSi$: C, 70.58; H, 3.72. Found: C, 69.89; H, 3.14.

II. Preparation of complexes

A. Synthesis of Complex (p-Tol)$CrBr_2(THF)_3$

Synthesis of Complex (p-Tol)$CrBr_2(THF)_3$ was performed using modified procedure published in (Daly, J. J.; Sneeden, R. P. A.; Zeiss, H. H. J. Am. Chem. Soc. 1966, 88, 4287-4288) from $CrCl_3$ and (p-Tol)MgBr in THF.

Anal. calcd. for $C_{19}H_{31}Br_2CrO_3$: C, 43.95; H, 6.02. Found: C, 43.81; H, 5.78.

B. Synthesis of Complex (ONN$^{Quin}$)$CrBr_2$(MeCN) (3a)

A Schlenk tube was charged with 0.150 g of 2a (0.269 mmol) and 0.140 g of (p-Tol)$CrBr_2(THF)_3$ (0.269 mmol), and 5 mL of toluene were vacuum transferred therein. The reaction mixture was stirred overnight at room temperature, evaporated and dried in vacuum. The deep-pink residue was recrystallised from 20-25 mL of dried acetonitrile to give 0.187 g (0.232 mmol) of 3a with a yield of 86%.

UV-vis ($CH_2Cl_2$, 298 K, $mol^{-l} \cdot dm^3 \cdot cm^{-1}$): $\epsilon_{527}$ 5660, $\epsilon_{500}$ 5296, $\epsilon_{371}$ 6455.

FAB-MS (m/z): $CHCl_3$: 1163.7 ($[L_2Cr]^+$).

μ(B.M.)=3.87.

Anal. calcd. for $C_{40}H_{30}Br_2CrN_3OSi$: C, 59.42; H, 3.74. Found: C, 58.65; H, 3.08.

Figure 7:
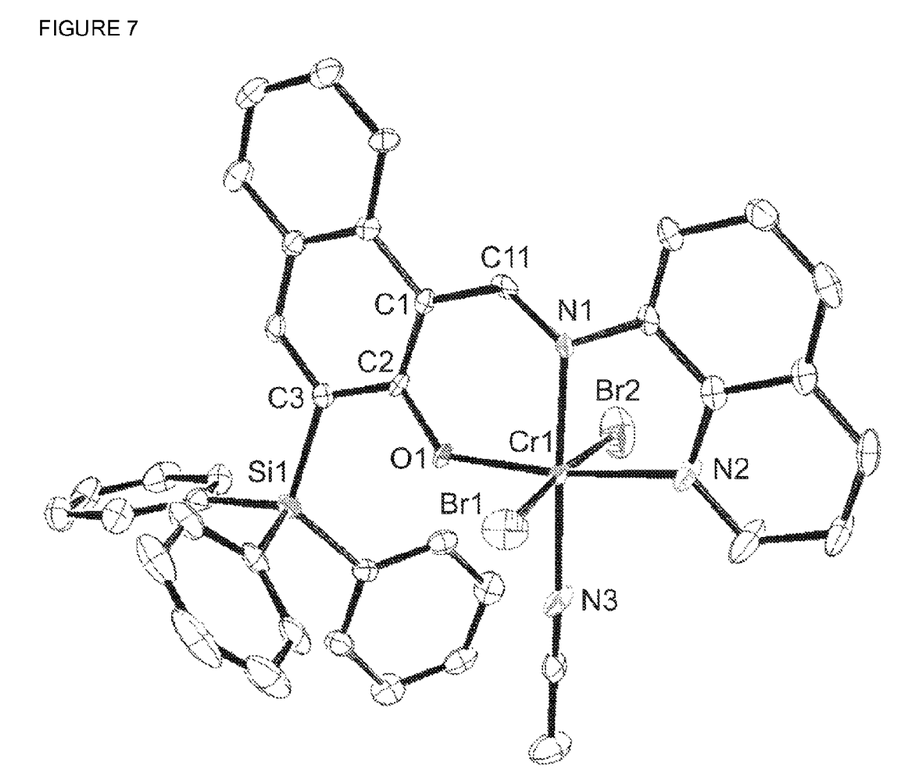

The molecular structure of the chromium complex is represented in FIG. 7.

C. Synthesis of Complex $(ONN^{P_y})CrBr_2(MeCN)$ (3b)

Following the same procedure as that used to prepare complex 3a, complex 3b was obtained from 0.100 g of 2b (0.192 mmol) and 0.100 g of (p-Tol)$CrBr_2(THF)_3$ (0.192 mmol) and isolated in an amount of 0.135 g (0.175 mmol) with a yield of 91%.

UV-vis ($CH_2Cl_2$, 298 K, $mol^{-1} \cdot dm^3 \cdot cm^{-1}$): $\epsilon_{496}$ 2865, $\epsilon_{319}$ 7384.

FAB-MS (m/z): $CHCl_3$: 1090.7 ($[ML_2]^+$); acetonitrile: 1090.6 ($[L_2Cr]^+$).

Anal. calcd. for $C_{37}H_{30}Br_2CrN_3OSi$: C, 57.52; H, 3.91. Found: C, 57.11; H, 3.13.

Figure 8:
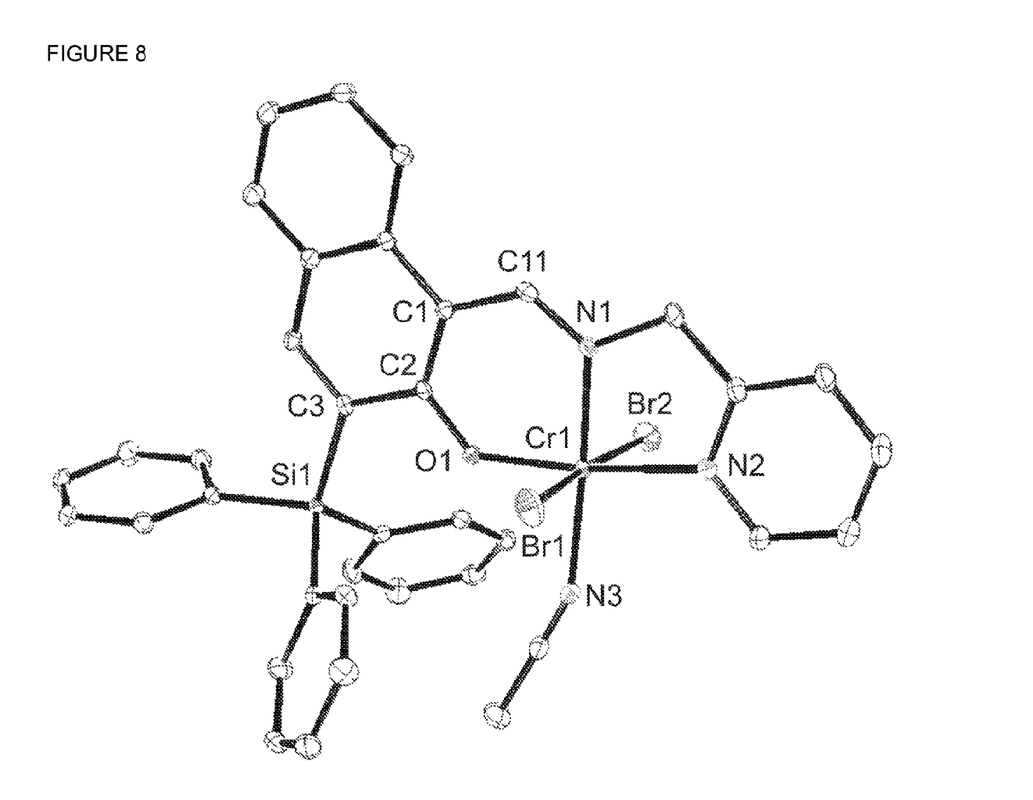
FIG. 8 represents the molecular structure of chromium complex 3b.
Figure 9:
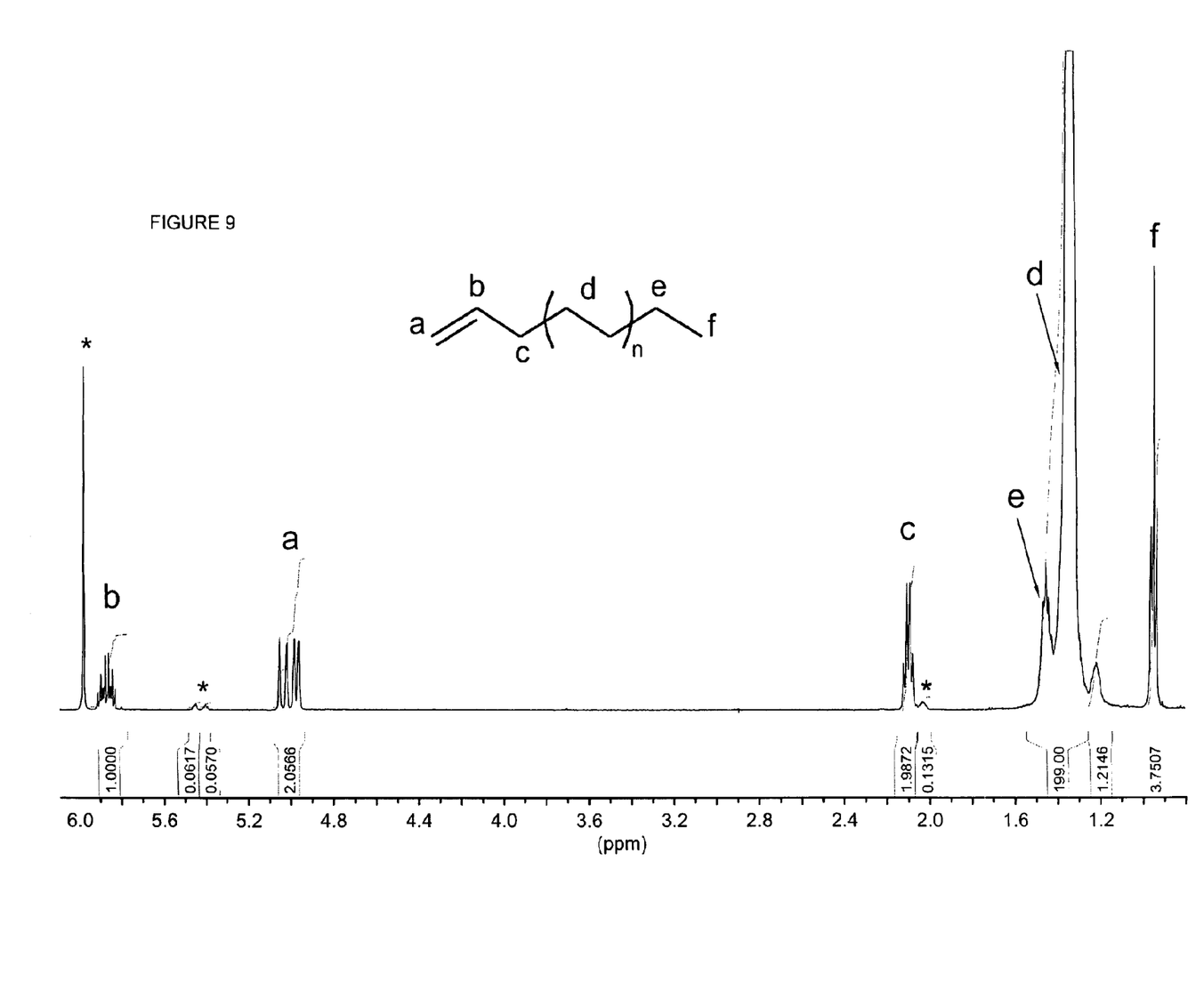
FIG. 9 represents a typical $^1$H NMR spectrum of vinyl end-capped oligoethylenes produced with the system 3a/MAO.
Figure 10:
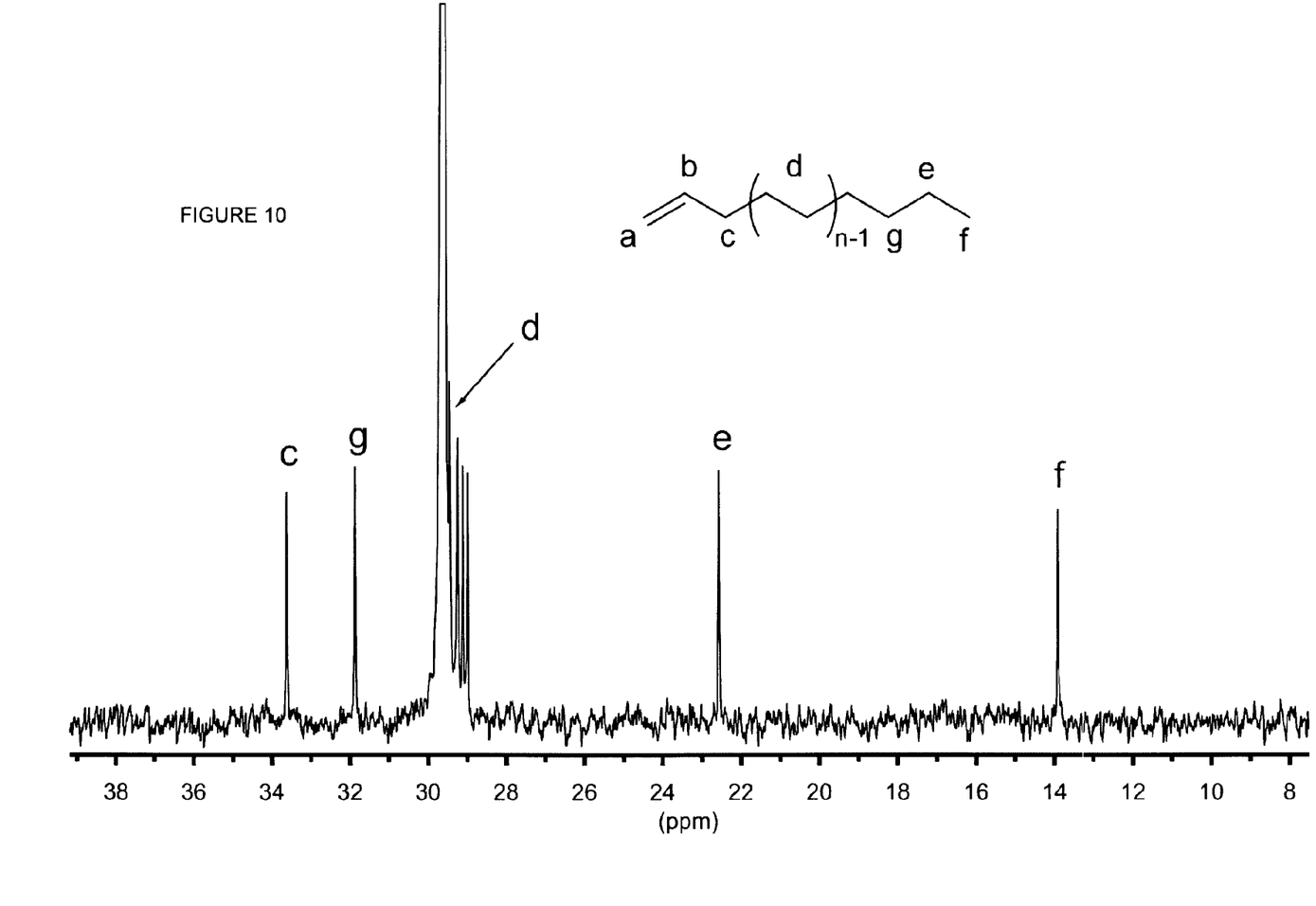
FIG. 10 represents a typical $^{13}$C NMR (high field region) spectrum of vinyl end-capped oligoethylenes produced with the system 3a/MAO.

The molecular structure of the chromium complex is represented in FIG. 8.

D. Synthesis of Complex $(ON-Ph^F)CrBr_2(MeCN)_2$ (3c)

Similarly complex 3c was prepared from 0.100 g of 2c (0.168 mmol) and 0.087 g of (p-Tol)$CrBr_2(THF)_3$ (0.168 mmol) and isolated in an amount of 0.101 g (0.114 mmol) with a yield of 68%.

UV-vis ($CH_2Cl_2$, 298 K, $mol^{-l} \cdot dm^3 \cdot cm^{-1}$): $\epsilon_{438}$ 6500, $\epsilon_{337}$ 10035, $\epsilon_{303}$ 9626.

FAB-MS (m/z): $C_2H_4Cl_2$: 1240.2 ($[L_2Cr]^+$).

μ(B.M.)=3.87.

Anal. calcd. for $C_{39}H_{27}Br_2CrF_5N_3OSi$: C, 52.72; H, 3.06. Found: C, 51.89; H, 2.78.

Homopolymerisation of Ethylene.

The polymerisation was carried out as follows.

A 300 mL glass high-pressure reactor was charged with 80 mL of freshly distilled toluene under argon flash. Mechanical stirring (Pelton turbine, 1000 rpm) was started, the reactor was then purged with ethylene and loaded with a solution of scavenger selected from MAO or DEAC, at atmospheric pressure, and then kept at the desired temperature by circulating water in a double wall. A solution of pre-catalyst in 2 mL of toluene was injected in by syringe. The gas pressure in the reactor was maintained immediately and kept constant with a back regulator throughout the experiment. The ethylene consumption was monitored via an Aalborg flowmeter. After a given time period, the reactor was depressurised and the reaction was quenched by adding about 5 mL of a 10% solution of HCl in methanol. The polymer was further precipitated by adding 500 mL of methanol, washed and dried in vacuum overnight at room temperature. The polymerisation conditions are summarised in Table I and the polymerisation results are presented in Table II.

Cat 1 was generated in situ from 2a and (p-Tol)$CrBr_2$(THF)$_3$
Cat 2 is generated in situ from 2b and (p-Tol)$CrBr_2$(THF)$_3$
Cat 3 is isolated complex 3a
Cat 4 is isolated complex 3b
Cat 5 is isolated complex 3c
The monomer was ethylene.

TABLE I

| Run | Cat | Amount cat (μmol) | Activator | Activator/M | $P_{C2H4}$ (bar) | T (° C.) | t (min) |
|---|---|---|---|---|---|---|---|
| 1 | cat 1 | 23 | MAO | 800 | 1 | 50 | 60 |
| 2 | cat 2 | 23 | MAO | 800 | 1 | 50 | 60 |
| 3 | cat1 | 5 | MAO | 500 | 6 | 50 (93)[a] | 10 |
| 4[b] | cat1 | 21 | MAO | 800 | 1 | 50 (93)[a] | 60 |
| 5 | cat 3 | 5 | DEAC | 500 | 6 | 50 | 60 |
| 6 | cat 3 | 5 | MAO | 500 | 6 | 50 (90)[a] | 10 |
| 7 | cat 3 | 5 | MAO | 500 | 1 | 50 | 20 |
| 8 | cat 3 | 5 | MAO | 500 | 6 | 25 (107)[a] | 5 |
| 9[c] | cat 3 | 5 | MAO | 500 | 6 | 50 (94)[a] | 10 |
| 10[d] | cat 3 | 5 | MAO | 500 | 6 | 50 (93)[a] | 10 |
| 11 | cat 4 | 5 | MAO | 500 | 6 | 50 (83)[a] | 10 |
| 12 | cat 5 | 5 | MAO | 500 | 6 | 50 | 60 |
| 13 | cat 5 | 5 | DEAC | 500 | 6 | 50 | 60 |

[a]The polymerisation reaction proceeded exothermally; the maximal temperature reached is given into brackets.
[b]MeCN (4 equiv. vs Cr) was added.
[c]THF (4 equiv. vs Cr) was added.
[d]Pyridine (4 equiv. vs Cr) was added.

TABLE II

| Run | Mass PE (g) | Productivity ($g_{polym}/g_{cata}$) | Activity (kgPE/mol/h) | $Mn^e$ (Da) | $M_n^f$ (Da) | $M_w/M_n^f$ | Vinyl[e] (mol %) | $T_m^g$ (° C.) |
|---|---|---|---|---|---|---|---|---|
| 1 | 3.50 | 270 | 151 | nd | 630 | 1.99 | <40 | 114 |
| 2 | 0.62 | 52 | 27 | 1430 | 800 | 2.10 | 67 | 119 |
| 3 | 9.22 | 2305 | 11060 | 1070 | nd | nd | 85 | 118 |
| 4 | 1.15 | 58 | 55 | 1130 | nd | nd | 90 | 116 |
| 5 | 0.11 | 27 | 22 | — | — | — | — | — |
| 6 | 11.80 | 2950 | 14160 | 1140 | 800 | 2.23 | 90 | 118 |
| 7 | 4.29 | 1072 | 2574 | 1450 | nd | nd | 90 | 119 |
| 8 | 9.89 | 2470 | 23730 | 1100 | nd | nd | 87 | 119 |
| 9 | 8.75 | 2190 | 10500 | 1320 | nd | nd | 88 | 118 |
| 10 | 12.43 | 3110 | 14900 | 1210 | nd | nd | 88 | 118 |
| 11 | 10.50 | 2760 | 12600 | 1340 | 850 | 2.22 | 91 | 122 |
| 12 | 0.20 | 45 | 40 | — | — | — | — | — |
| 13 | traces | — | — | — | — | — | — | — |

[e]Determined from the $^1$H NMR spectrum in $C_2D_2Cl_4$ at 100° C.
[f]Determined by GPC at 150° C. in trichlorobenzene vs polystyrene standards.
[g]Determined by DSC.

The invention claimed is:

1. A pro-ligand of formula I or its tautomeric form of formula I' wherein $R^1$, $R^3$, $R^4$, $R^5$, $R^6$ and $R^7$ are each independently selected from hydrogen, unsubstituted or substituted hydrocarbyl, or inert functional group, wherein two or more of said groups can be linked together to form one or more rings, Z is an atom selected from group 14 of the Periodic Table, each $R^2$ is independently selected from a substituted or unsubstituted aryl group having at most 8 carbon atoms, and/or an alkyl group, with the restriction that $Z(R^2)_3$ is a bulky group, at least as bulky as tertio-butyl, $R^8$ is $CH_2$-(2-pyridyl), alpha-quinolone or $C_6F_5$, possibly containing donor atoms.

2. The pro-ligand of claim 1, wherein $R^1$, $R^3$, $R^4$, $R^5$, $R^6$ and $R^7$ are each independently selected from hydrogen or alkyl group having at most 6 carbon atoms.

3. The pro-ligand of claim 1, wherein Z is C or Si.

4. The pro-ligand of claim 1, wherein the donor atoms are halogens or atoms selected from groups 15 and 16 of the periodic Table.

5. The pro-ligand of claim 1, wherein all $R^2$ are the same substituted or unsubstituted phenyl group, higher aromatic group or alkyl having at most 10 carbon atoms.

6. The pro-ligand of claim 5, wherein $R^2$ is unsubstituted phenyl group or tertio-butyl group.

7. A process for preparing a pro-ligand of formula I or its tautomeric form of formula I' wherein $R^1$, $R^3$, $R^4$, $R^5$, $R^6$ and $R^7$ are each independently selected from hydrogen, unsubstituted or substituted hydrocarbyl, or inert functional group, wherein two or more of said groups can be linked together to form one or more rings, Z is an atom selected from group 14 of the Periodic Table, each $R^2$ is independently selected from a substituted or unsubstituted aryl group having at most 8 carbon atoms, and/or an alkyl group, with the restriction that $Z(R^2)_3$ is a bulky group, at least as bulky as tertio-butyl, $R^8$ is a unsubstituted or substituted, aliphatic or aromatic hydrocarbyl group, possibly containing donor atoms, the process comprising:

providing 2-methoxynaphthalene of formula reacting the 2-methoxynaphthalene with $(R^2)_3ZX'$, wherein X' is an halogen, in the presence of sec-BuLi in a solvent to obtain a first compound of formula reacting the first compound with N-bromosuccinimide to obtain a second compound of formula reacting the second compound with DMF in the presence of tert-BuLi (two equivalents) in a solvent to obtain a third compound of formula deprotecting the third compound in order to obtain a fourth compound of formula condensation of the fourth compound with the appropriate amine R⁸—NH$_2$ in the presence of catalytic amounts of an acid, to obtain compounds of formula I and its tautomeric form I'

8. The process of claim 7, wherein the acid is HCOOH or p-toluenesulfonic acid (PTSA).

9. A metallic complex of formula II wherein M is a metal Group 6 of the periodic Table, each X is the same or different and is an alkyl, benzyl substituted or not, aryl substituted or not, amido, alkoxide, and/or halide and wherein L² is a solvent; and wherein $R^3$, $R^4$, $R^5$, $R^6$ and $R^7$ are each independently selected from hydrogen, unsubstituted or substituted hydrocarbyl, or inert functional group, wherein two or more of said groups can be linked together to form one or more rings, wherein Z is an atom selected from group 14 of the Periodic Table, wherein each $R^2$ is independently selected from a substituted or unsubstituted aryl group having at most 8 carbon atoms, and/or an alkyl group, with the restriction that $Z(R^2)_3$ is a bulky group, at least as bulky as tertio-butyl, and wherein $R^8$ is a unsubstituted or substituted, aliphatic or aromatic hydrocarbyl group, possibly containing donor atoms.

10. The metallic complex of claim 9, wherein either X are all the same and are Br, or one X is para-tolyl and the other X is Br.

11. A process for preparing the metallic complex of 21 comprising complexing the ligand of claim 1 with metallic salt MX$_n$, in a solvent, wherein n is 2.

12. A catalyst system comprising the metallic complex of claim 9 and an activating agent having an ionising action selected from aluminium alkyl, aluminoxane or boron containing agents.

13. A process for oligo-, homo- or co-polymerising ethylene and alpha-olefins comprising:
   injecting the catalyst system of claim 12 into a reactor;
   injecting ethylene and optional comonomer into the reactor;
   maintaining the reactor under polymerisation conditions to form oligomers or polymers; and
   retrieving the oligomers and/or polymer.

14. The process of claim 13 further comprising introducing comonomer selected from propylene or 1-hexene.

* * * * *